United States Patent
Chaudhary et al.

(10) Patent No.: US 9,968,295 B2
(45) Date of Patent: May 15, 2018

(54) SURGICAL GUIDANCE AND PLANNING SOFTWARE FOR ASTIGMATISM TREATMENT

(71) Applicant: NOVARTIS AG, Basel (CH)

(72) Inventors: Gautam Chaudhary, Laguna Hills, CA (US); Jack T. Holladay, Bellaire, TX (US); Melvin Sarayba, Keller, TX (US); Hadi Srass, Pomona, CA (US)

(73) Assignee: Novartis AG, Basel (CH)

( * ) Notice: Subject to any disclaimer, the term of this patent is extended or adjusted under 35 U.S.C. 154(b) by 534 days.

(21) Appl. No.: 14/312,187

(22) Filed: Jun. 23, 2014

(65) Prior Publication Data

US 2015/0046094 A1 Feb. 12, 2015

Related U.S. Application Data

(60) Provisional application No. 61/863,018, filed on Aug. 7, 2013.

(51) Int. Cl.
| | |
|---|---|
| *A61B 18/20* | (2006.01) |
| *A61B 5/00* | (2006.01) |
| *A61B 3/10* | (2006.01) |
| *A61F 9/007* | (2006.01) |
| *A61F 2/16* | (2006.01) |
| *G06F 19/00* | (2018.01) |

(52) U.S. Cl.
CPC .............. *A61B 5/4851* (2013.01); *A61B 3/10* (2013.01); *A61F 2/1645* (2015.04); *A61F 9/007* (2013.01); *A61B 2505/05* (2013.01); *A61F 2240/002* (2013.01); *G06F 19/3481* (2013.01)

(58) Field of Classification Search
None
See application file for complete search history.

(56) References Cited

U.S. PATENT DOCUMENTS

| | | | |
|---|---|---|---|
| 2004/0054358 A1* | 3/2004 | Cox | .................... A61F 9/00806 606/5 |
| 2010/0152847 A1 | 6/2010 | Padrick et al. | |
| 2011/0092984 A1 | 4/2011 | Tripathi | |
| 2012/0172854 A1* | 7/2012 | Raymond | ............... A61F 9/008 606/5 |
| 2013/0018276 A1 | 1/2013 | Zaldivar et al. | |

FOREIGN PATENT DOCUMENTS

JP 2009045461 A 3/2009

OTHER PUBLICATIONS

PCT/US2014/044246, International Search Report and Written Opinion of the International Searching Authority, PCT Nternational Searching Authority, dated Nov. 14, 2014, 8 pgs.

* cited by examiner

*Primary Examiner* — Anna Skibinsky

(57) ABSTRACT

Software for calculating an astigmatism treatment is operable upon execution to perform the following steps: receiving an initial primary incision position; determining a power and orientation for a toric intraocular lens (IOL) to treat an astigmatism of an eye based on the initial primary incision position; determining an adjusted primary incision position based on the power and the orientation for the toric IOL to further reduce the astigmatism; and generating an output comprising the adjusted primary incision position.

5 Claims, 9 Drawing Sheets

FIG. 5

| Name, Case1, Case1 | ID | DOB. 10-Oct 1950 |

Patient Locator  PreOp Exam  IOL Calc  | Astigmatism Planner |  Surgery Data  PostOp Exam  Toric PostOp Surgeon: James, Smith     PreOp Date: 05/30/2013         [3]
[6]  Ref:          VTX: 12.00      Target Rx: 0.00
     BCVA          UCVA           AL (Opt): 23.00
     Flat K: 40.00@20   Steep K: 41.80@110    Astigm: +1.80@110
Lens from Active Lens List: SN60WF(Std Phaco) ▼                 [1&2]
     SIA 0.75    Pri Inc. Loc: 180    Sec1: 45    Sec2:
Post SIA Flat K: 39.689@14°  Steep K: 42.111@104°  Astigm.: 2.423@104°
IOL 0.00: [◄]  [▶] RI 100.00    Parameter Pref.
     RI1: 47.6°@104°  RI2: 47.6°@284°  Depth: 80%  Diam: 9.0mm  ← [4]
Formula: Holladay II ▼                                    [5]
              Alcon SN60WF
              Procedure: Std. Phaco
              MFG* ACD (Opt): 5.57 pACD=5.18
       90     IOL SEO    SEO Ref.
  135     45   25.50      0.53
               25.00      0.18      Relaxing incision length
 180      0    26.25      0.90      recommendation
               26.50     -0.17
               27.00     -0.53
  225    315   Lens       Res. Astigm.
       270     SN60WF     +0.00Dx104°
Pri Inc. 2.4mm @180°

IOL Placement Axis:      104°
IOL Ideal Toricity:      0.00D@IOL
Expected Residual Rx:    -0.175+0.000D
Expected Post Op Flat K: 40.900@14°  Steep K: 40.900  Astigm.: 0.000

FIG. 7

| Name, Case1, Case1 | ID | DOB. 10-Oct 1950 |

Patient Locator  PreOp Exam  IOL Calc  | Astigmatism Planner |  Surgery Data  PostOp Exam  Toric PostOp Surgeon: James, Smith                PreOp Date: 05/30/2013
Ref:                     VTX: 12.00         Target Rx: 0.00
BCVA:                    UCVA               AL (Opt): 23.00
Flat K: 40.00@20         Steep K: 41.80@110   Astigm: +1.80@110

Lens from Active Lens List: SN6ATx (Std Phaco) ▼   ← Toric IOL implant

SIA 0.75  |  Pri Inc. Loc: 180  |  Sec1: 45  |  Sec2:
Post SIA Flat K: 39.689@14°  Steep K: 42.111@104°  Astigm.: 2.423@104°

IOL 100.00: [◄   ▬▬▬   ►]  RI 0.00 | Optimize. | Parameter Pref.
RI1:          RI2:              Depth: 80%  Diam: 9.0mm        ← "Sliding Bar" set at 100% IOL Formula: Holladay II ▼

Alcon SN6ATx
Procedure: Std. Phaco
MFG* ACD (Opt): 5.75  pACD=5.35

| IOL SEO | SEO Ref. |
| --- | --- |
| 26.00 | 0.45 |
| 26.50 | 0.11 |
| 26.65 | 0.00 |
| 27.00 | -0.25 |
| 27.50 | -0.60 |

| Lens | Res. Astigm. |
| --- | --- |
| SN6AT3 | +1.34Dx104° |
| SN6AT4 | +0.81Dx104° |
| SN6AT5 | +0.29Dx104° |
| SN6AT6 | +0.24Dx14° |  ← Toric IOL recommendation
| SN6AT7 | +0.76Dx14° |
| SN6AT8 | +1.29Dx14° |
| SN6AT9 | +1.82Dx14° |

Pri Inc. 2.4mm @180°    IOL @104°

IOL Placement Axis:     104°
IOL Ideal Toricity:     3.41D@IOL
Expected Residual Rx:   -0.015+0.239Dx14°
Expected Post Op Flat K: 39.689@14°  Steep K: 42.111  Astigm.: 2.423

FIG. 10

| Name, Case1, Case1 | ID | DOB. 10-Oct 1950 |

Patient Locator   PreOp Exam   IOL Calc   | Astigmatism Planner |   Surgery Data   PostOp Exam   Toric PostOp Surgeon: James, Smith          PreOp Date: 05/30/2013
Ref:                  VTX: 12.00          Target Rx: 0.00
BCVA:                 UCVA                AL (Opt): 23.00
Flat K: 40.00@20    Steep K: 41.80@110   Astigm: +1.80@110

Lens from Active Lens List: SN6ATx (Std Phaco) ▼

[ SIA 0.75 ]  [ Pri Inc. Loc: 180 ]  [ Sec1: 45 ]  [ Sec2: ]

Post SIA Flat K: 39.689@14°   Steep K: 42.111@104°   Astigm.: 2.423@104°

[ IOL 29.37: ◄    ►  ]  RI 70.63     [ Parameter Pref. ]

[ RI1: 35.4°@104°   RI2: 35.4°@284° ]   Depth: 80%   Diam: 9.0mm

Formula: Holladay II ▼

Alcon SN6ATx
Procedure: Std. Phaco
MFG* ACD (Opt): 5.75  pACD=5.35

| IOL SEO | SEO Ref. |
|---|---|
| 26.00 | 0.45 |
| 26.50 | 0.11 |
| 26.65 | 0.00 |
| 27.00 | -0.25 |
| 27.50 | -0.60 |

| Lens | Res. Astigm. |
|---|---|
| SN6AT0 | +0.70Dx104° |
| SN6AT2 | +0.00Dx104° |
| SN6AT3 | +0.35Dx14° |
| SN6AT4 | +0.87Dx14° |
| SN6AT5 | +1.40Dx14° |

Pri Inc. 2.4mm @180°    IOL @104°

IOL Placement Axis:     104°
IOL Ideal Toricity:     1.00D@IOL
Expected Residual Rx:   +0.105+0.001D
Expected Post Op Flat K: 40.544@14°   Steep K: 41.256   Astigm.: 0.712

Toric IOL implant

Move the "Sliding Bar" to be in between 100% IOL and 100% RI

New RI length recommendation

New Toric IOL recommendation

SURGICAL GUIDANCE AND PLANNING SOFTWARE FOR ASTIGMATISM TREATMENT

This application claims the priority of U.S. Provisional application No. 61/836,018 filed Aug. 7, 2013.

TECHNICAL FIELD

The present invention relates generally to surgical guidance and planning software for astigmatism treatment, and more particularly, to a method and system for determining astigmatism treatment with toric intraocular lenses and incisions.

BACKGROUND

The human eye functions to provide vision by refracting light through a clear outer portion called the cornea, and refracting the light by way of a crystalline lens onto a retina. The quality of the focused image depends on many factors including the size and shape of the eye, and the transparency of the cornea and the lens. When age or disease causes the lens to become aberrated, vision deteriorates because of the loss of retinal image quality. This loss of optical quality in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a portion of the anterior capsule is removed and a thin phacoemulsification cutting tip is inserted into the diseased lens and vibrated ultrasonically. The vibrating cutting tip liquefies or emulsifies the nucleus and cortex of the lens so that the lens may be aspirated out of the eye. The diseased nucleus and cortex of the lens, once removed, is replaced by an artificial lens in the remaining capsule (in-the-bag). In order to treat corneal astigmatism, the IOL may be toric. The power selection for the IOL can also take into account the effect of incisions in the corneal shape (astigmatism) through which the IOL is injected, as described in greater detail in U.S. Pat. No. 7,476,248, which is incorporated herein by reference.

An alternative treatment for corneal astigmatism is the use of limbal relaxing incisions (LRIs), which are typically opposed arcuate incisions in the cornea that reshape the cornea to correct astigmatism. While the term "limbal relaxing incision" or "LRI" is used in this specification, because the incisions are typically made at the limbus and therefore conventionally described this way, the term should be understood to include any corneal relaxing incision, referring generally to any incision that does not penetrate the cornea and that is positioned to adjust the astigmatism of the cornea. Based on statistical samples of surgical outcomes, two commonly used nomograms, the Donnenfeld nomogram and the Nickamin nomogram, have been developed to guide surgeons in performing LRIs. The Donnenfeld nomogram takes into account age (relatively to average age for cataract patients), incision location and pattern, and whether the astigmatism is with the rule or against the rule. The Nickamin nomogram considers age and degree of astigmatism more granularly than the Donnenfield nomogram. These nomograms can be further customized based on the surgeon's actual surgical outcomes.

SUMMARY

In a first embodiment, software for calculating an astigmatism treatment is operable upon execution to perform the following steps: receiving an initial primary incision position; determining a power and orientation for a toric intraocular lens (IOL) to treat an astigmatism of an eye based on the initial primary incision position; determining an adjusted primary incision position based on the power and the orientation for the toric IOL to further reduce the astigmatism; and generating an output comprising the adjusted primary incision position.

In a second embodiment, software for calculating an astigmatism treatment is operable upon execution to perform the following steps: receiving biometric information for a patient; determining based on the biometric information an astigmatic correction comprising at least one of (a) a position for one or more limbal relaxing incisions and (b) a power and an orientation for a toric intraocular lens (IOL); generating an output comprising the astigmatic correction; receiving a selection of a different ratio of astigmatic correction attributable to the one or more limbal relaxing incisions and the toric IOL; determining an updated astigmatic correction including at least one of (a) an updated position for the one or more limbal relaxing incisions and (b) an updated power and/or orientation of the toric IOL.

Of course, those skilled in the art will appreciate that the present invention is not limited to the above features, advantages, contexts or examples, and will recognize additional features and advantages upon reading the following detailed description and upon viewing the accompanying drawings.

BRIEF DESCRIPTION OF THE DRAWINGS

FIGS. 5-10 illustrate an example graphical user interface (GUI) according to various embodiments of the present invention.

DETAILED DESCRIPTION

Figure 1:
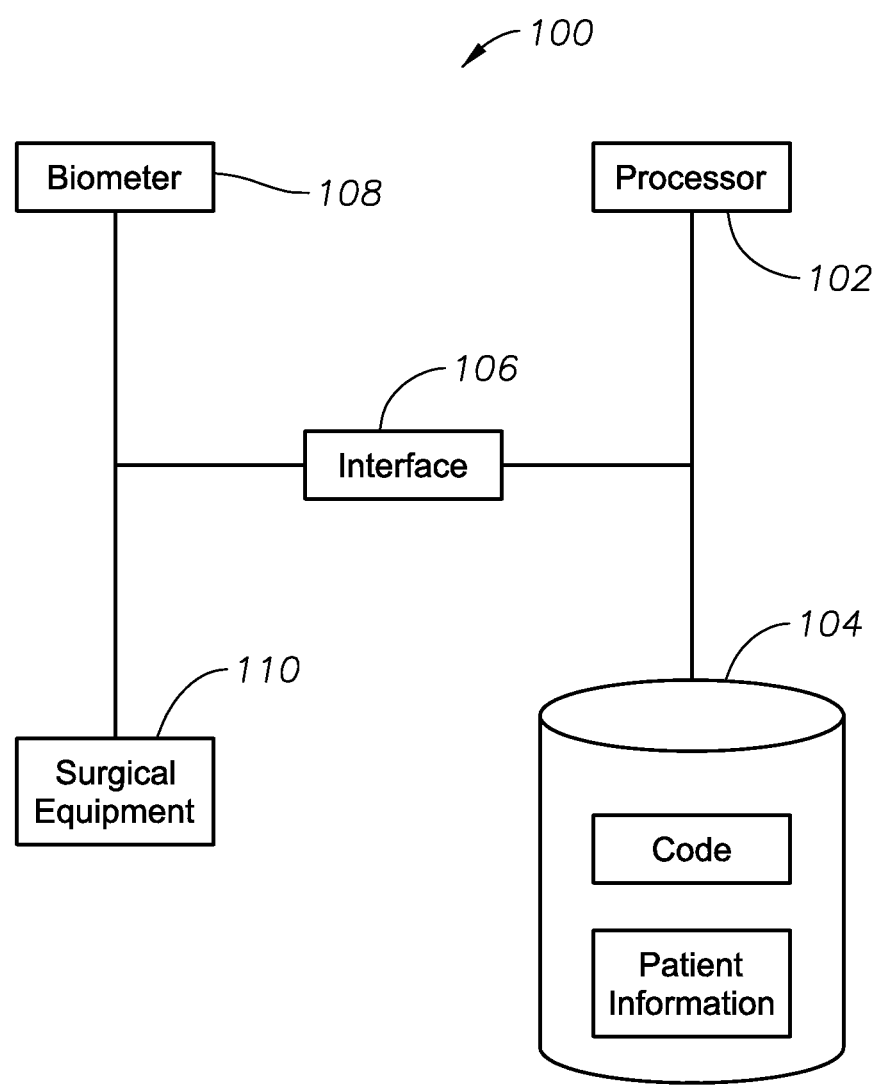
FIG. 1 illustrates an example system for surgical guidance and planning suitable for use with various embodiments of the present invention.

Various embodiments of the present invention provide improved methods and systems for surgical planning that advantageously addresses both toric IOL power and incisions. In particular, these methods and systems can use predict a combined treatment to reduce the overall astigmatism in the post-surgical patient's overall optical system more nearly to zero. The output provided by these systems will be referred to herein as a "predicted astigmatic correction" to indicate that this would be the expected correction produced by the combination of incisions and/or the toric IOL. When the term "optimized" is used in the context of this description, it refers to the surgical astigmatism being reduced as nearly to zero as possible within the range of the treatment parameters that are being varied within given ranges. This may be influenced, for example, by the restrictions given by the surgeon, who may prefer to make incisions on one side or within one quadrant, thus restricting the available range of incision locations. These may also be influenced by the increments of cylindrical power in which a selected toric IOL are available, so that, for example, the toric IOL selection must be made in half-diopter increments.

In certain embodiments, methods and systems for surgical planning may provide integrated surgical planning that provide a combined calculation for both toric IOL and LRI calculations. In other aspects, methods and systems for surgical planning may provide options to allocate a certain degree of astigmatism correction to each component of the astigmatic treatment, allowing the surgeon to select from a variety of treatment options using different toric IOLs and LRI techniques. Such options may include varying the length, depth, position and/or number of LRIs as well as the power and orientation of the toric IOL. In still other aspects, methods and systems for surgical planning may receive a primary incision and secondary incision locations, referring to the incision through which the IOL will be inserted as well as irrigation, aspiration and other instruments necessary for the cataract operation, and then may determine a combination of toric IOL power and orientation along with an adjusted incision placement so that the combination of the toric IOL and the incisions provide an improved treatment.

As described herein, any such methods and systems can be implemented in software, hardware, and/or firmware, and the various functions can be distributed among multiple components, such as biometers for collecting patient information and ophthalmic surgical equipment used in performance of surgical procedures for correcting astigmatism (including but not limited to surgical microscopes and laser systems for incising the cornea, lens capsule or crystalline lens). Implementations may also include the use of programmable electronic computing devices, such as desktop or laptop personal computers, electronic tablets, personal digital assistants, or smart phones, loaded with appropriate software. It should therefore be understood that the various examples described herein can be suitably modified in numerous other usable combinations.

FIG. 1 illustrates an example system 100 suitable for use with various embodiments of the present invention. System 100 includes a processor 102, a memory 104, an interface 106, a biometer 108 and surgical equipment 110. Processor 102 may be any microprocessor, microcontroller, programmable element, or other device or collection of devices for processing electronically stored instructions (software or firmware) to perform any of the various information processing functions described herein. Memory 104 may be any suitable form of volatile or non-volatile information storage accessible by processor 102, including but not limited to optical, electronic, or magnetic media. Interface 106 represents any electronic component allowing exchange of information with a person (referred to herein as a "user" of system 100) or between the components of system 100. User interfaces suitable for communication with persons may include any known input device for computers, including a touch screen, keyboard, switch, knob, pedal, button, pointing device, or other similar component. Interface 106 may likewise include any suitable visible and/or audible output, such as a monitor and/or speaker, for communication of information to the user, which may display a graphical user interface ("GUI") to allow the user to operate system 100. Interface 106 may also include any suitable electronic components for exchanging information with other electronic devices (including wireless signals), such as other components of system 100, according to any programmed information exchange protocol.

Biometer 108 is any suitable device for taking anatomical measurements of a patient's eye using, for example, optical or ultrasound measurements. Such anatomical measurements may include without limitation the axial length of the eye, anterior chamber depth, crystalline lens thickness, corneal diameter (white-to-white distance) and the anterior and/or posterior curvature of the cornea. Surgical equipment 110 may include any form of equipment suitable for use in performing surgical procedures for the correction of astigmatism that includes suitable electronic components for intercommunication with other components of system 100, including but not limited to surgical microscopes and laser systems for incising the cornea, lens capsule or crystalline lens.

Code 120 represents instructions stored in memory 104 executed by processor 102 to perform various functions of system 100. As noted previously, various embodiments of the present invention provide improved methods and systems for surgical planning that include both toric IOLs and incisions. Thus, in operation, various embodiments of the system 100 include techniques for planning surgery capable of addressing astigmatism based on certain information. Patient information 122 represents all stored information concerning the astigmatism treatment for a specific patient, which may include, without limitation, biometry information taken from biometer 108 and surgeon-specific information that may be stored from previous surgical planning or may be input as part of the planning process.

EXAMPLE 1

Figure 2:
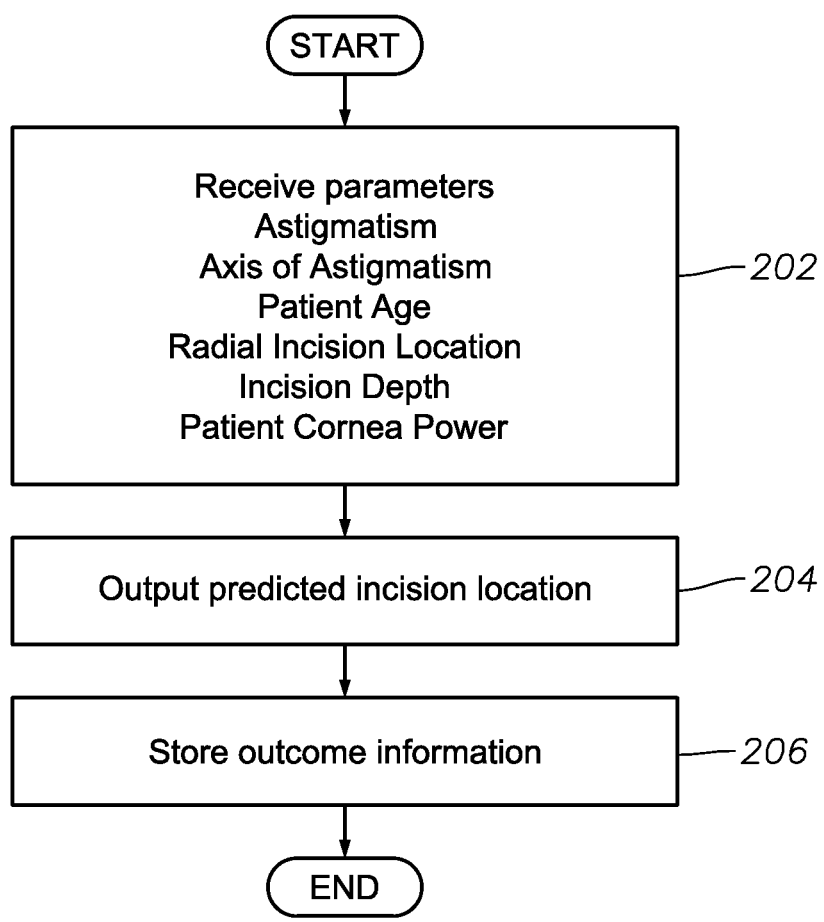
FIG. 2 illustrates a flow chart for providing a predicted astigmatic correction with an optimized limbal relaxing incision (LRI) position.

In one example of a method of operation, FIG. 2 illustrates a flow chart 200 for providing a predicted astigmatic correction with an optimized LRI position. In general, system 100 may determine LRI position based on multiple additional aspects of the patient as compared to prior nomogram techniques. At step 202, system 100 receives via interface 106 (or calculates from stored information) the following six parameters: (1) the astigmatism to be treated, (2) the axis of astigmatism, (3) patient age, (4) a surgeon-specific treatment zone (radial location of the incision), (5) a surgeon-specific LRI depth as a percentage of the patient's maximum corneal thickness, and (6) the patient specific corneal power. For purposes of this specification, "receives" in the context of patient-specific information shall refer generically both to receiving information from a user or from another device via the interface as well as deriving or calculating the specified information from other information that has been received in this manner. These represent a minimum number of factors to be considered, but additional factors can be added to the determination. For example, the location of the primary incision and/or any secondary incisions, including radial and angular location and angular span (arc length), can also be considered.

At step 204, system 100 then outputs a predicted incision location for one or more LRIs that reduces the astigmatism as nearly to zero as possible given the expected resolution of the incision placement. In particular embodiments, the predicted incision location may also vary one or more of the angular span (arc length), radial position, and number of incisions. In certain embodiments, the relative arc length, number or arrangement of the incisions can be adjusted so that; for example, the arc length of one incision may be larger than that of an opposed incision. A factor of 1.5-2.0 in particular may be useful for balancing the relative effects of the opposed LRIs. In certain embodiments including calculations of the primary incision, the primary incision location can be adjusted, and the predicted incision location can also be updated based on the adjusted primary incision. Empirical studies and additional surgeon-specific results can further tailor the resulting nomogram for a particular system 100 and particular surgeon so that the predicted incision information can more accurately minimize the relevant astigmatism. This is illustrated at step 206, wherein system 100 stores surgical outcome information correlated with the predicted incision location.

EXAMPLE 2

Figure 3:
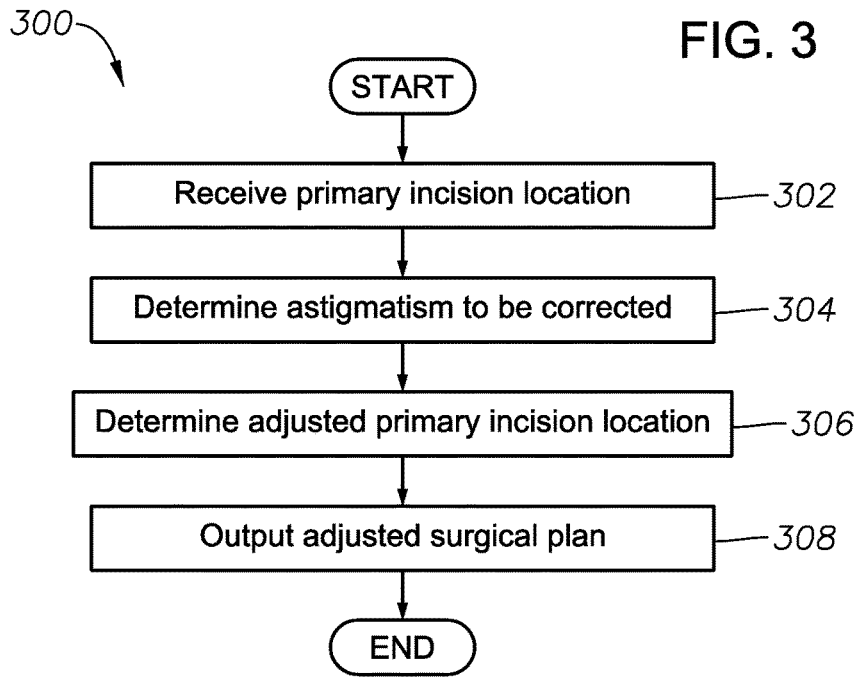
FIG. 3 illustrates a flow chart for providing an optimized primary incision location.

In a second example, FIG. 3 shows a flow chart 300 for providing an optimized primary incision location. At step 302, system 100 receives a primary incision location, which may include radial and angular position as well as surgeon-specific factors such as a predicted surgically induced astigmatism. At step 304, system 100 determines the astigmatism to be corrected for the patient, which may be based on calculations made by system 100 from patient biometry measurements or which may alternatively be information about a selected toric IOL that has been previously calculated. Based on the initial primary incision location, at step 306, system 100 determines an adjusted incision location and/or toric IOL position so that the astigmatism is reduced relative to the initial primary incision location. This results from the surgical astigmatism that is produced by the primary incision being changed, so that the net effect of the toric IOL and the surgically induced astigmatism from the primary incision can more nearly reduce the net post-surgical astigmatism in the patient's optical system to zero.

In alternative embodiments, the user can input the different primary incision location, and system 100 can calculate an updated toric IOL power and position in response to the input. In some embodiments, the power of the toric IOL may also be adjusted based on the incremental cylindrical power steps for the selected toric IOL. Thus, for example, it might be more advantageous to use a toric IOL with less cylindrical power or with a different orientation if the adjusted primary incision location provides a greater degree of astigmatism correction.

At step 308, system 100 outputs an adjusted surgical plan with the adjusted primary incision position and the adjusted toric IOL position and/or power, if applicable. If LRIs are also a component of the astigmatism treatment, then these incision positions may also be updated, including angular position, angular span (arc length), radial position, and/or number of incisions. In certain embodiments, the relative arc length, number or arrangement of the incisions can be adjusted so that; for example, the arc length of one incision may be larger than that of an opposed incision. A factor of 1.5-2.0 in particular may be useful for balancing the relative effects of the opposed LRIs. In general, system 100 can optimize the surgical plan through a combination of toric IOL power and orientation, primary incision placement, and LRI placement to reduce astigmatism as close to zero as possible.

EXAMPLE 3

Figure 4:
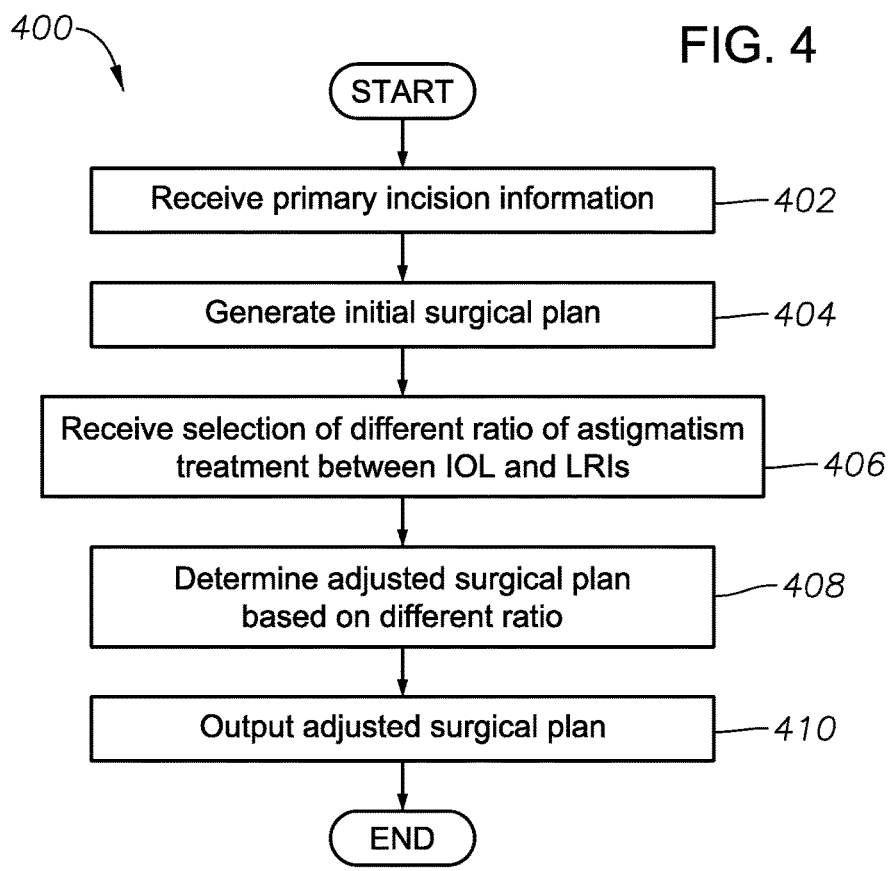
FIG. 4 illustrates a flow chart for providing interactive calculation of astigmatism treatment using toric intraocular lenses (IOLs) and incision.

In a third example, FIG. 4 shows a flow chart 400 for providing interactive calculation of astigmatism treatment using toric IOLs and incisions. At step 402, system 100 receives initial primary incision information, which may include radial and angular position information as well as surgeon-specific factors such as a predicted surgically induced astigmatism. At step 404, system 100 generates an initial surgical plan. The surgical plan includes a radial location for the primary incision and one or more LRIs as well as a toric IOL power and orientation. At step 406, system 100 receives a user selection of a different ratio of astigmatism treatment between the toric IOL and the LRI. For example, the user may select a certain percentage of the patient's astigmatism to be corrected by the IOL and the remainder to be corrected by the LRIs. Alternatively, the user could consider cases where the astigmatism would be entirely corrected by either the IOL or the LRIs. At step 408, system 100 determines an adjusted surgical plan based on the different ratio, and then outputs the adjusted surgical plan at step 410. In certain embodiments, the relative arc length, number or arrangement of the incisions can be adjusted so that; for example, the arc length of one incision may be larger than that of an opposed incision. A factor of 1.5-2.0 in particular may be useful for balancing the relative effects of the opposed LRIs.

Importantly, the foregoing examples are not intended to be exclusive of one another. For instance, all three examples can be implemented with the formula of the first example. Likewise, all three examples can adjust primary incision locations, and all three examples can allow for adjustment of the ratio of astigmatism correction between the toric IOL, primary incision, and LRIs. Thus, these features should not be understood as exclusive of one another.

Software Interface

Figure 6:
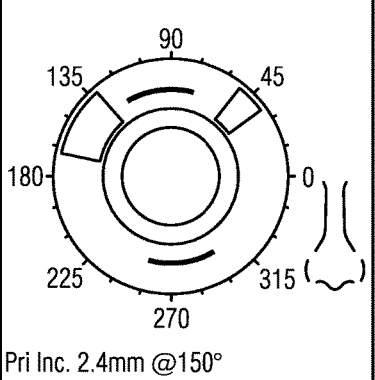

FIGS. 5-10 illustrate an example GUI incorporating all three of the examples presented herein. While this example is not based on values for an actual patient, the operation is illustrated in the same manner as it would be for an actual patient. In FIGS. 5-10, the six parameters provided in the first example are illustrated with corresponding numbers. FIG. 5 shows an example LRI-only treatment based on the six patient factors. The predicted incision location includes an angular location and span (arc length) for the LRIs. FIG. 6 illustrates an adjustment in the primary incision location, which in turn adjusts the surgically induced astigmatism and the LRI position. In FIGS. 5-6, only LRIs are being used to treat astigmatism; the IOL is not toric.

FIGS. 7-10 illustrate a "slider bar" input allowing the user to select a different ratio between the astigmatism treatment provided by the toric IOL and LRIs. This is one of any number of possible examples for the GUI for selection of the ration, including without limitation numerical entry fields (which may also include up/down arrows), knob icons, radio buttons with specified ratio increments (e.g., cylindrical power increments for the toric IOL), or any other conceivable GUI interface for adjustment of the ratio. In FIG. 7, the treatment provided is 100% attributed to the toric IOL, taking into account the surgically induced astigmatism of the primary incision. The toric IOLs are denominated as SN6ATx, where x increases with the amount of cylinder power (T0 being zero cylindrical correction, i.e., a non-toric IOL). The residual astigmatism in this case is 0.24 diopters at 14 degrees based on a selection of the toric IOL model resulting in the lowest residual astigmatism.

Figure 8:
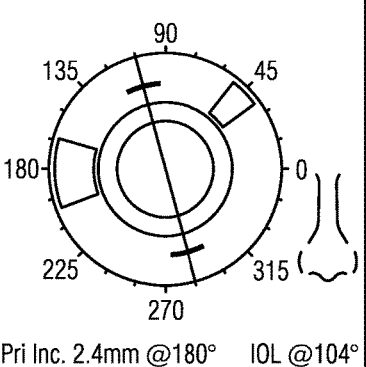
Figure 9:
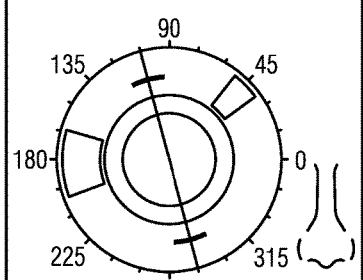

In FIG. 8, the slider bar has been adjusted so that the ratio of astigmatism treatment is only 66.07% attributable to the toric IOL, and the adjusted surgical plan includes LRI positions to correct the remaining 33.93% of the patient's astigmatism. A lower power toric IOL model has been selected, and now the residual astigmatism with the LRIs is zero. In FIG. 9, the ratio is adjusted to increase the percentage attributable to the LRIs, producing an increase in the angular span (arc length) of the LRIs and a further reduction in the toric IOL power. This again results again in zero astigmatism. Lastly, in FIG. 10, over 70% of the correction is attributable to the LRIs, producing an even lower toric IOL power with slightly longer LRIs. Note that even a non-toric IOL results in only 0.70 diopters of residual astigmatism, illustrating that almost all astigmatism correction results from the LRIs.

The preceding description of various embodiments was given for purposes of illustration and example. Those skilled in the art will appreciate, of course, that the present invention may be carried out in other ways than those specifically set forth herein without departing from essential characteristics of the invention. In particular, features of the various embodiments are intended to be freely combined with one another in any combination, unless the features are explicitly or apparently exclusive of one another, and any such features can be generalized to any level of intermediate combination. The present embodiments are thus to be considered in all respects as illustrative and not restrictive, and all changes coming within the meaning and equivalency range of the appended claims are intended to be embraced therein.

What is claimed is:

1. An apparatus, comprising:
    one or more processing modules operable to execute software embodied in a non-transitory computer-readable medium, the software operable when executed to perform the following steps:
        receiving an initial primary incision position;
        receiving a surgically induced astigmatism value corresponding to the initial primary incision position;
        determining, based on an amount of astigmatism to be corrected for an eye and the surgically induced astigmatism value corresponding to the initial primary incision position, a power and orientation for a toric intraocular lens (IOL);
        determining, based on an amount of post-surgical astigmatism associated with the toric IOL having the determined power and orientation and the surgically induced astigmatism value corresponding to the initial primary incision position, an adjusted primary incision position, wherein a surgically induced astigmatism value corresponding to the adjusted primary incision position reduces the amount of post-surgical astigmatism; and
        generating an output comprising the adjusted primary incision position; and
    a laser system communicatively coupled to the one or more processing modules, the laser system operable to:
        receive the output comprising the adjusted primary incision position; and
        in response to receiving the output, incise a cornea of a patient to create the primary incision at the adjusted primary incision position.

2. The apparatus of claim 1, wherein the software is further operable when executed to receive at least one secondary incision position, wherein the step of determining the power and the orientation of the toric IOL is also based on the at least one secondary incision position.

3. The apparatus of claim 1, wherein:
    the software is further operable when executed to determine a position for at least one limbal relaxing incision based on the power and the orientation for the toric IOL and generate an output comprising the position for the at least one limbal relaxing incision; and
    the laser system is further operable to:
        receive the output comprising the position for the at least one limbal relaxing incision; and
        incise the cornea of the patient to create the at least one limbal relaxing incision.

4. The apparatus of claim 1, wherein the amount of astigmatism to be corrected for the eye is determined based on patient biometric data retrieved from a memory.

5. The apparatus of claim 4, wherein:
    the apparatus further comprises a biometer operable to generate the patient biometric data; and
    the patient biometric data is imported into the memory from the biometer via an interface.

* * * * *